US00PP10376P

United States Patent [19]

Hesse

[11] Patent Number: Plant 10,376

[45] Date of Patent: May 5, 1998

[54] CHRYSANTHEMUM PLANT NAMED 'ORANGE STATE'

[75] Inventor: Peter S. Hesse, Nipomo, Calif.

[73] Assignee: Clearwater Nursery, Inc., Nipomo, Calif.

[21] Appl. No.: 711,856

[22] Filed: Sep. 12, 1996

[51] Int. Cl.[6] ..... A01H 5/00

[52] U.S. Cl. ..... Plt./82.3

[58] Field of Search ..... Plt./82.3

*Primary Examiner*—Howard J. Locker

*Attorney, Agent, or Firm*—Arnold, White & Durkee

[57] ABSTRACT

The present invention comprises a new and distinct cultivar of Chrysanthemum, botanically known as *Dendranthema grandiflora* and referred to by the cultivar name Orange State.

1 Drawing Sheet

BACKGROUND OF THE NEW PLANT

Orange State was found as a natural orange mutation (sport) of the variety Golden State (U.S. Plant Pat. No. 8,694) by Peter S. Hesse in a controlled growing environment at Clearwater Nursery, Nipomo, Calif. 93444, U.S.A. This mutation was discovered as one flowering shoot within a flowering bench of the seedling Golden State, in March of 1992.

The first set of asexual reproduction of Orange State was accomplished when vegetative cuttings were taken in June 1992, in a controlled environment in Nipomo, Calif. by Peter S. Hesse.

Horticultural examination of controlled flowerings of successive plantings has shown that the unique combination of characteristics as herein disclosed for Orange State are firmly fixed and are retained through successive generations of asexual reproduction.

Orange State has not been observed under all possible environmental conditions. The phenotype may vary significantly with variations in the environment such as temperature, light intensity and daylength.

The following observations, measurements and comparisons describe plants grown in a controlled environment in Nipomo, Calif. Unrooted cuttings were directly stuck into 6.5" pots and grown under the natural temperature and daylength prevailing in January through March of 1996.

The following traits have been repeatedly observed and are determined to be basic characteristics of Orange State, which in combination distinguish this Chrysanthemum as a new and distinct cultivar.

1. Flat capitulum form.
2. Anemone capitulum type.
3. Orange fully expanded outer ray florets.
4. Orange anemone disc with green eye.
5. Diameter across the face of capitulum of 9.3 cm.
6. Exceptional upright to spreading habit with an average of 4.0 breaks after a single pinch.
7. Flowering response is approximately 58 days from the start of short days.
8. Relatively easy to control plant height on the bench such that the finished height will range from 14 inches to 18 inches depending on pot size and market requirements.

DESCRIPTION OF THE PHOTOGRAPHS

The accompanying photographic drawing shows typical inflorescence and leaf characteristics of Orange State, with the colors being as nearly true as possible with illustrations of this type.

Sheet 1 is a color photograph of Orange State grown as a pinched spray pot mum with 5 cuttings in a 6.5" pot.

Color designations are made with respect to the 1986 edition of R.H.S. Colour Chart, first published in 1986 by The British Royal Horticultural Society, London, England. The B-Nine™ growth regulator referred to in the culturing procedures is 2,2-dimethylhydrazide sold under the name of Daminozide or Alar, manufactured by Uni Royal.

Of the commercial cultivars known to the inventor, the most similar in form, color, and habit to Orange State is the parent cultivar Golden State. Chart A compares certain characteristics of Orange State to the same characteristics of Golden State. The plants were grown side by side in a controlled greenhouse environment. Growth regulator B-Nine™ was applied at 2,500 ppm in 3 applications. Comparisons were made in November, 1992 in Nipomo, Calif.

TABLE A

| | GOLDEN STATE | ORANGE STATE |
|---|---|---|
| CAPITULUM FORM | FLAT | FLAT |
| CAPITULUM TYPE | ANEMONE | ANEMONE |
| DIAMETER ACROSS FACE OF CAPITULUM | 6.5 CM | 9.3 CM |
| BRANCHING PATTERN | UPRIGHT AND SPREADING | UPRIGHT SPREADING |
| BREAKS/PINCH | 5.0 | 4.0 |
| HEIGHT IN A 6.5" POT | 14–18 INCHES | 14–18 INCHES |
| DISC FLORET COLOR | EDGE BEGIN W/9A GRADUATING TO YELLOW GREEN 144A | MOSTLY ORANGE GRADUATING TO YELLOW GREEN 144A |
| # DISC FLORETS | 171 | 219 |
| LENGTH OF DISC FLORETS | 1.43 CM | 1.04 CM |
| RAY FLORET COLOR | FRONT: GOLDEN YELLOW 9A BACK: PALE YELLOW 8A | FRONT: GREYED-ORANGE 163B BACK: GREYED-ORANGE 163D |
| # RAY FLORETS | 19 | 20.6 |
| SHAPE OF RAY FLORETS | ELLIPTIC | ELLIPTIC |

TABLE A-continued

| | GOLDEN STATE | ORANGE STATE |
|---|---|---|
| LENGTH OF RAY FLORETS | 3.6 CM | 4.4 CM |
| WIDTH OF RAY FLORETS | 1.09 CM | 1.4 CM |
| # OF FLOWERS/ BREAK | 6.75 | 6.8 |
| LEAF COLOR | FRONT: 147A BACK: 147B | 147Q UPPER 147B LOWER |
| MATURE LEAF LENGTH | UP TO 12.5 CM | UP TO 11.2 CM |
| MATURE LEAF WIDTH | AVERAGE 8.8 CM | AVERAGE 8.8 CM |
| RESPONSE/TREATMENT | 8.5 WEEKS medium vigorous grower | 8.5 WEEKS medium vigorous grower |

Traits of the 2 cultivars are similar with respect to the large flat, anemone capitulum and a similar upright, spreading branching pattern and similar number of breaks per pinch per plant and a finished height that is about the same. Each also has a similar number of ray florets and leaf color and dimension. The response time of 8.5 weeks from the start of short days is the same for both plants. However, the diameter of the capitulum of Orange State may be larger than the capitulum of Golden State and the disc floret color of Orange State is orange with a green eye, while it is golden yellow with a green eye for Golden State. Orange State tends to have more disc florets than Golden State. The length of the disc florets is smaller for Orange State. The front Ray floret color for Orange State is greyed-orange 163 B, while for Golden State the floret color is yellow 9A. The back ray floret color of Orange State is greyed-orange 163D, for Golden State it is pale yellow 6A. The ray florets of both cultivars are elliptic. Orange State has ray florets that are longer than Golden State. The width of the ray florets is greater for Orange State.

The Plant

Classification:

*Botanical.*—*Dendranthema grandiflora* CV. name Orange State.

*Commercial.*—Flat anemone to be grown primarily as a Spray/CBR (center bud removed) or disbud pot mum.

Inflorescence:

*Capitulum.*—Form: Flat. Type: Anemone. Diameter across face: average of 9.3 cm. Disc diameter (fully mature): 2.2 cm.

*Corolla of ray florets.*—Color (general tonality from a distance of three meters): Orange. Color: Front fully expanded ray floret: 163 B. Back fully expanded ray floret: 163 D. Disc floret color. Edge begins with 163 B. Center green of 144 A.

General appearance:

*Height.*—When grown in a 6.5" pot with 1–4 applications of B-Nine at a rate of 2500 ppm, the total plant height from the bottom of the pot may be maintained at 14 to 18 inches.

*Branching pattern.*—Upright and spreading with an average of 4.0 breaks when grown with one pinch.

*Foliage.*—Color (upper surface): 147 A. Color (lower surface): 147 B. Shape: See photograph coarsely divided.

*Reproductive organs.*—Gynoecium: Present in ray and disc florets. Androecium: Present in disc floret only. Pollen: Scant.

What is claimed is:

1. A new and distinct chrysanthemum plant named 'Orange State' substantially as herein described and shown characterized by its orange ray floret coloration.

* * * * *

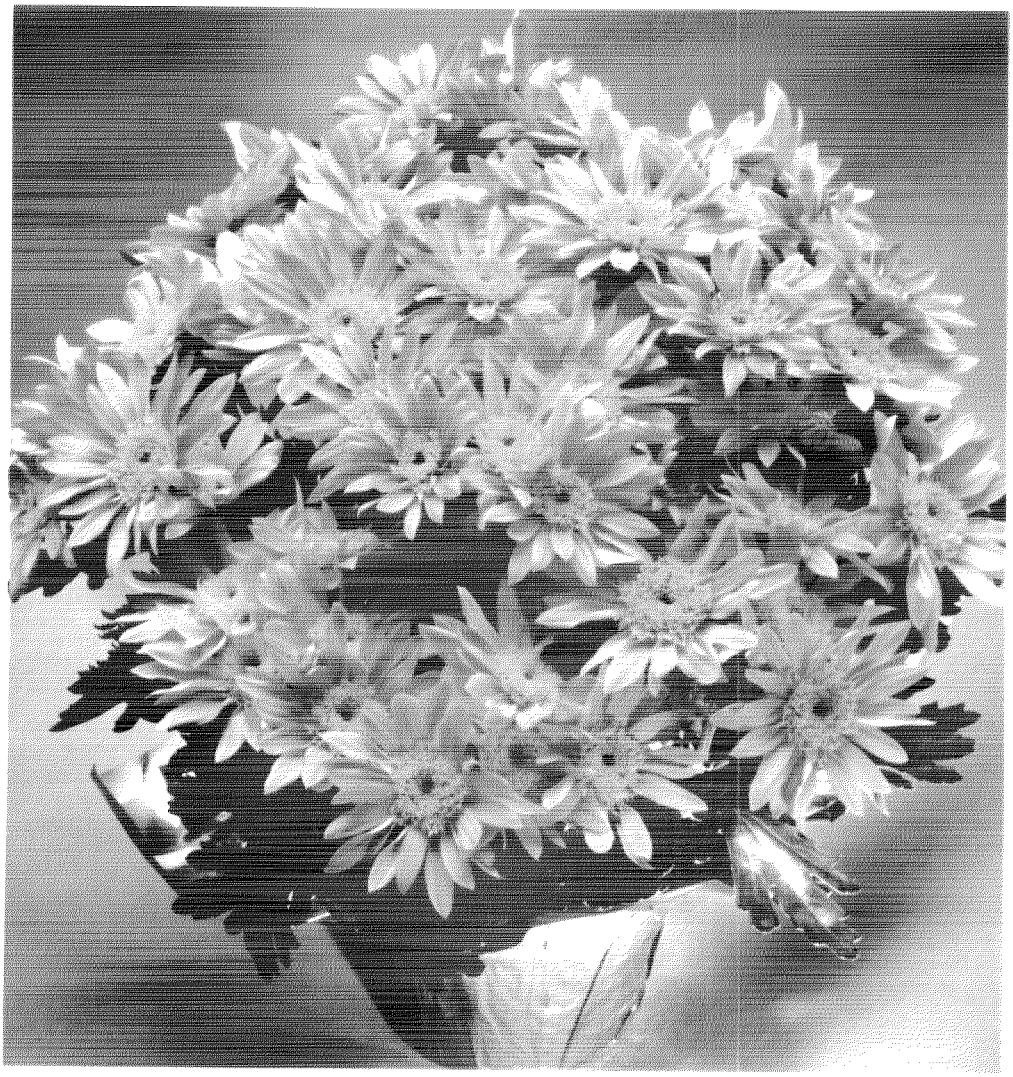

UNITED STATES PATENT AND TRADEMARK OFFICE

CERTIFICATE OF CORRECTION

PATENT NO. : PP10376

DATED : May 5, 1998

INVENTOR(S) : PETER S. HESSE

It is certified that error appears in the above-identified patent and that said Letters Patent is hereby corrected as shown below:

In Column 3, Table A-continued, under Leaf Color for 'Orange State', please delete "147Q" and insert therefor --147A--.

Signed and Sealed this

Twenty-seventh Day of October, 1998

*Attest:*

Bruce Lehman

BRUCE LEHMAN

*Attesting Officer*

*Commissioner of Patents and Trademarks*